United States Patent
Lewis

(10) Patent No.: US 6,546,812 B2
(45) Date of Patent: Apr. 15, 2003

(54) VENTURI FLOWMETER FOR USE IN AN EXHAUST SAMPLING APPARATUS

(76) Inventor: Gary W. Lewis, 15 Beaulieu La., Foothill Ranch, CA (US) 92610

( * ) Notice: Subject to any disclaimer, the term of this patent is extended or adjusted under 35 U.S.C. 154(b) by 0 days.

(21) Appl. No.: 09/854,340

(22) Filed: May 11, 2001

(65) Prior Publication Data

US 2002/0189369 A1 Dec. 19, 2002

(51) Int. Cl.⁷ .............................................. G01F 1/44
(52) U.S. Cl. ................................. 73/861.63; 73/863.2
(58) Field of Search ................... 73/861.63, 863.02, 73/863.03, 863.11, 23.24, 23.31

(56) References Cited

U.S. PATENT DOCUMENTS

| | | | |
|---|---|---|---|
| 3,699,814 A | * 10/1972 | Kaufman | 73/863.11 |
| 3,817,100 A | * 6/1974 | Anderson et al. | 73/861.63 |
| 4,240,294 A | 12/1980 | Grande | 73/861.47 |
| 4,249,164 A | 2/1981 | Tivy | 73/861.08 |
| 4,406,161 A | 9/1983 | Locke et al. | 73/118.1 |
| 4,481,828 A | 11/1984 | Cheng | 73/861.63 |
| 4,586,367 A | 5/1986 | Lewis | 73/23.33 |
| 4,660,408 A | 4/1987 | Lewis | 73/28.06 |
| 4,787,251 A | 11/1988 | Kolodjski | 73/725 |
| 4,823,591 A | 4/1989 | Lewis | 73/1.26 |
| 5,184,501 A | 2/1993 | Lewis et al. | 73/23.31 |
| 5,187,972 A | * 2/1993 | DeFriez | 73/23.2 |
| 5,199,306 A | 4/1993 | Hunter | 73/861.63 |
| 5,347,843 A | 9/1994 | Orr et al. | 73/861.52 |
| 5,365,795 A | 11/1994 | Brower, Jr. | 73/861.65 |
| 5,423,226 A | 6/1995 | Hunter et al. | 73/861.63 |
| 5,736,650 A | 4/1998 | Hiron et al. | 73/861.63 |
| 5,837,903 A | * 11/1998 | Weigand | 73/861.42 |
| 5,886,267 A | 3/1999 | Ortiz | 73/861.61 |
| 5,968,452 A | 10/1999 | Silvis | 73/863.03 |
| 6,016,711 A | 1/2000 | Ullman et al. | 73/863.03 |
| 6,058,787 A | 5/2000 | Hughes | 73/861.63 |
| 6,122,980 A | 9/2000 | Lewis et al. | 73/863.43 |

* cited by examiner

Primary Examiner—Harshad Patel
(74) Attorney, Agent, or Firm—Eric Karich

(57) ABSTRACT

An apparatus for sampling the emission content of an exhaust gas from an exhaust source has an exhaust inlet adapted for connecting the exhaust source with a venturi metering device for measuring the flow rate of the exhaust gas. The venturi metering device includes a housing having an entrance section, a throat section, and an exit section, the throat section having a smaller diameter than the entrance and exit sections. The housing includes first and second pressure transducers that produce an electrical output that characterizes the pressure that the pressure sensing means senses, the electrical outlet enabling a computer of the venturi metering device to accurately measure the pulsating flow of the exhaust gas in both directions.

16 Claims, 3 Drawing Sheets

VENTURI FLOWMETER FOR USE IN AN EXHAUST SAMPLING APPARATUS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates generally to a venturi flowmeter, and more particularly to a venturi flowmeter for use in an exhaust sampling apparatus.

2. Description of Related Art

Under present day federal regulations, the exhaust emissions from motor vehicles must not exceed specified values of certain constituent contaminants, as set forth in the Code of Federal Regulations. See Title 40 of the Code of Federal Regulations, Parts 81–99, Subparts A, B, D, E, F, G, K and N. See also Kaufman U.S. Pat. No. 3,699,814. The presence of such standards has made it imperative that the exhaust emissions from vehicle engines be tested and analyzed to determine the relative amount of certain constituents therein. Much effort has gone into the development of equipment for use in this field of exhaust gas sampling, and it is now known to deliver exhaust gases from an internal combustion engine at an accurately controlled flow rate through a test apparatus for purposes of determining and analyzing the relative amounts of constituents therein. The general scheme of such testing is to add dilution air to the exhaust gases. The total volume of the mixture of exhaust and dilution air must be measured. A continuously proportional sample of volume must be collected and is stored for subsequent analysis of constituents such as hydrocarbons, carbon monoxide, and $NO_x$. Mass emissions are determined from the sample concentrations and total flow over the test period.

One such system for analyzing samples from exhaust gases is set forth in U.S. Pat. No. is 3,699,814 to Kaufman entitled, "Gas Sampler," issued Oct. 24, 1972. The Kaufaman patent, the disclosure of which is incorporated herein by reference, taught a much improved gaseous exhaust emission sampler which replaced the constant displacement pump of prior systems with a critical flow venturi and centrifugal blower for metering the diluted exhaust emissions at a constant volume flow.

Another system utilizes a pair of critical flow venturis for proportional sampling. An example of such a system is set forth in U.S. Pat. No. 3,817,100. In another such system, a downstream pump produces a sufficient vacuum on the bulkstream critical flow venturi exit so that the bulkstream mixture is flowing at sonic velocity, a condition which limits the bulkstream mixture to a constant mass flow rate at a given set of upstream temperature and pressure conditions measured at the bulkstream critical flow venturi inlet. A sample is extracted from the dilute bulkstream flow through another critical flow venturi in close proximity to the bulkstream critical flow venturi so that the venturis are operating under the same inlet pressure and temperature conditions. This sample critical flow venturi operates in connection with a downstream pump in the sampling line to create sonic flow, and thereby a constant mass flow rate at the measured upstream temperature and pressure conditions. Thus, the sample critical flow venturi extracts a sample for analysis at a flow rate proportional to the bulkstream flow rate.

Although the flow rate controlled by a critical flow venturi will vary a small amount due to changes in the venturi inlet temperature and pressure, if the sample venturi and bulkstream venturi are operating at critical flow rate conditions at identical inlet pressure and temperature conditions, the sample flow rate is extracted in proportion to the bulkstream flow rate.

The state of the art in this field is represented by Lewis et al., U.S. Pat. Nos. 5,184,501 and 6,122,980, and Lewis, U.S. Pat. Nos. 4,586,367, 4,660,408, and 4,823,591 ("the Lewis references"). The Lewis references teach various embodiments of an exhaust sampling apparatus that use venturi flowmeters to measure the flow of an exhaust gas through the apparatus. However, the venturi flowmeters disclosed in the Lewis references do not measure reverse flow rates, so are therefore never positioned adjacent to the exhaust source, as in the present invention.

The prior art, including the Lewis references, also teaches the calculation of an average pressure; and the square root of the average pressure is then used to calculate the average flow rate. As described herein, this methodology is acceptable using prior art systems; however, this methodology introduces unacceptable errors when the venturi metering device is positioned adjacent to the exhaust source.

The prior art does teach a flowmeter that can measure reverse flow rates. Ortiz, U.S. Pat. No. 5,886,267, teaches a measuring system for measuring the flow of a liquid through a conduit such as an irrigation system. The system includes pressure transducers in an arrangement similar to the present invention. However, the Ortiz device is designed for use in a different field, and therefore does not teach many of the structures of the present invention. Ortiz does not teach the inclusion of temperature sensors for calculating the mass flow rate of an exhaust gas. Ortiz also does not teach the use of heaters for preventing the flow of liquids through the flowmeter.

The prior art teaches various venturi metering devices for measuring the flow rate of a gas through the device. However, the prior art does not teach a venturi metering device adapted for measuring the flow rate of a pulsing exhaust gas immediately adjacent an exhaust source. The present invention fulfills these needs and provides further related advantages as described in the following summary.

SUMMARY OF THE INVENTION

The present invention teaches certain benefits in construction and use which give rise to the objectives described below.

The present invention provides an apparatus for sampling the emission content of an exhaust gas from an exhaust source. The apparatus includes an exhaust inlet adapted for connecting the exhaust source with a venturi metering device for measuring the flow rate of the exhaust gas. The venturi metering device includes a housing having an entrance section, a throat section, and an exit section, the throat section having a smaller diameter than the entrance and exit sections. The housing includes a pressure sensing means for sensing the pressure in the throat section and the entrance section, and for producing an electrical output that characterizes the pressure that the pressure sensing means senses, the electrical output enabling a computer of the venturi metering device to accurately measure the pulsating flow rate of the exhaust gas in both directions through the housing.

A primary objective of the present invention is to provide an apparatus for sampling the emission content of an exhaust gas from an exhaust source, the apparatus having advantages not taught by the prior art.

Another objective is to provide a venturi metering device that can take rapid, accurate readings of the flow rate of an exhaust gas without introducing errors caused by the pulsation of the exhaust gas often found adjacent the exhaust source.

A further objective is to provide a more accurate method of calculating the average flow rate of the exhaust gas.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

Figure 1:
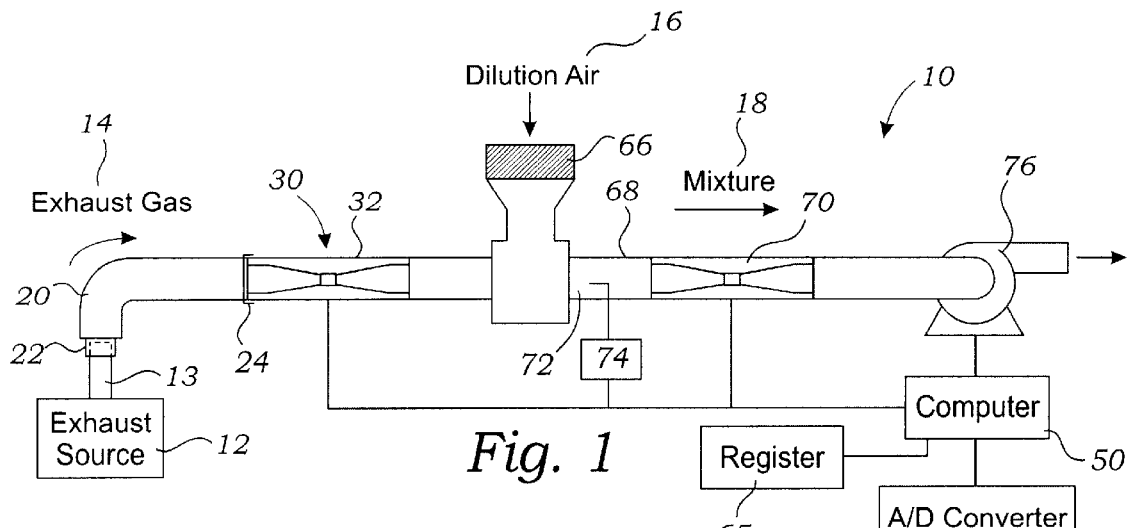
FIG. 1 is a diagrammatic illustration of an apparatus for sampling the emission content of an exhaust gas from an exhaust source.

The above described drawing figures illustrate the invention, an apparatus 10 for sampling the emission content of an exhaust gas 14 from an exhaust source 12. As shown in FIG. 1, the apparatus 10 includes an exhaust inlet 20 adapted for connection with the exhaust source 12, the exhaust inlet 20 being attached to a venturi metering device 30 for measuring the flow of the exhaust gas 14 from the exhaust source 12. A dilution air inlet 66 is adapted to be connected with an exit section 38 of the venturi metering device 30 to provide a mixture 18 of exhaust gas 14 and dilution air 16. The mixture 18 flows into a flow confining path 68 for establishing a flow of the mixture 18 from the dilution air inlet 66 to a flow rate measuring means 70 for measuring the flow rate of the mixture 18, the flow confining path 68 including a sampling zone 72. The apparatus 10 further includes a sampling means 74 for extracting a sample of the mixture 18 flowing through the sampling zone 72.

As shown in FIG. 1, the exhaust inlet 20 is a conduit adapted for connecting the exhaust source 12 with the venturi metering device 30. The exhaust inlet 20 includes a tailpipe adapter 22 at one end and a venturi adapter 24 at the other end. The tailpipe adapter 22 is designed for coupling the exhaust inlet 20 to tailpipe 13 of the exhaust source 12, generally an internal combustion engine of an automobile. The exhaust inlet 20 itself is a conduit constructed to withstand the high temperature of the exhaust gas 14 and direct the exhaust gas 14 into the venturi metering device 30.

Figure 2:
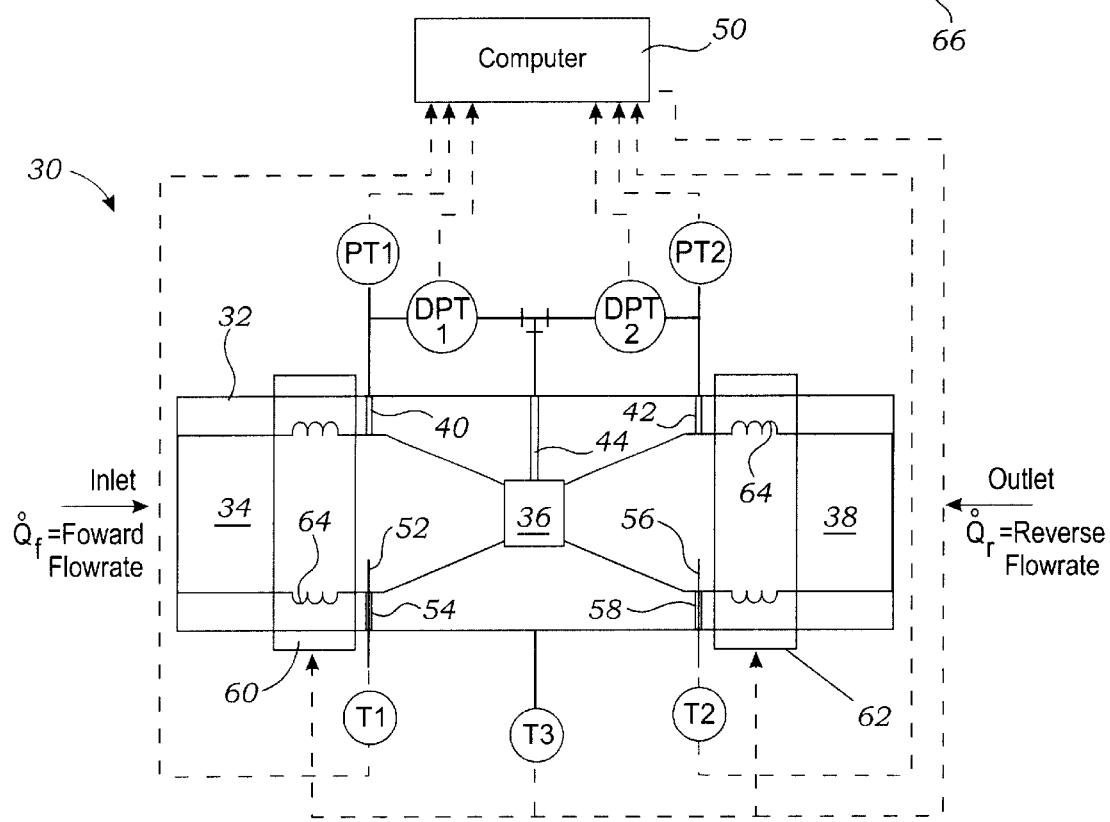
FIG. 2 is a diagrammatic illustration of a venturi metering device utilized in the apparatus.

As shown in FIG. 2, the venturi metering device 30 includes a housing 32 having a longitudinal axis, an entrance section 34, a throat section 36, and an exit section 38, the throat section 36 having a smaller diameter than the entrance and exit sections 38. The entrance and exit sections 34 and 38 are preferably symmetrical about the throat section 36, although this is not required for the function of the venturi metering device 30.

The entrance and exit sections 34 and 38 include a pressure sensing means for sensing the pressure in the throat section 36 and the entrance section 34, and for producing an electrical output that characterizes the pressure that the pressure sensing means senses, the electrical output enabling a computer 50 of the venturi metering device 30 to accurately measure the pulsating flow rate of the exhaust gas 14 in both directions through the housing 32. This is an important feature because many exhaust sources 12 emit the exhaust gas 14 in pulses that sometimes result in a reverse flow of the exhaust gas 14. It is critical to the accuracy of the venturi metering device 30 that reverse flows be measured and included in the overall flow calculation. The entrance section 34 is adapted for connection with the exhaust inlet 20. The exit section 38 is adapted for connection with the dilution air inlet 66, as described below.

While we state that the pressure sensing means senses pressure at the entrance and throat sections 34 and 36, this is expressly considered to include the equivalent arrangements, described in greater detail below, including measurements at the throat and exit sections 36 and 38, and also including measurements at the entrance, throat, and exit sections 34, 36, and 38. Also, it is possible for the housing 32 to be asymmetrical as long as the pressure sensing means is properly calibrated to take into account any asymmetries in the shape of the housing 32.

In the preferred embodiment, shown in FIG. 1, the pressure sensing means includes a first pressure transducer PT1, a second pressure transducer PT2, a first differential pressure transducer DPT1, and a second differential pressure transducer DPT2. The first pressure transducer PT1 is in fluid communication with the entrance section 34 through an entrance conduit 40, although direct placement of the first pressure transducer PT1 within the entrance section 34 is also possible in an equivalent alternative embodiment. The second pressure transducer PT2 is in fluid communication with the exit section 38 through an exit conduit 42 that is similar to the entrance conduit 40.

The first differential pressure transducer DPT1 is operably positioned to sense the difference in pressure between the entrance section 34 and the throat section 36. The second differential pressure transducer DPT2 is operably positioned to sense the difference in pressure between the throat section 36 and the exit section 38. To facilitate the operation of the first differential pressure transducer DPT1 and the second differential pressure transducer DPT2, the housing 32 includes a throat conduit 44 in fluid communication with the throat section 36.

The first and second pressure transducers PT1 and PT2, and the first and second differential pressure transducer DPT1 and DPT2, are operatively connected to the computer 50 for electronically reporting their measurements. The computer 50 can then calculate the flow rate through the venturi metering device 30 using techniques well known in the art.

Not all of the above-described sensors are required for the operation of the venturi metering device 30. It is possible for the computer 50 to calculate many of the values determined by one or more of the above-described sensors, thus removing the requirement of including one of the first and second pressure transducers PT1 and PT2, and one of the first and second differential pressure transducers DPT1 and DPT2. Some of the alternative embodiments that can be devised are described below. These alternative embodiments are meant to be illustrative of some of the combinations that can be devised by those skilled in the art, and should not be considered a comprehensive list of all potential embodiments.

Figure 4:
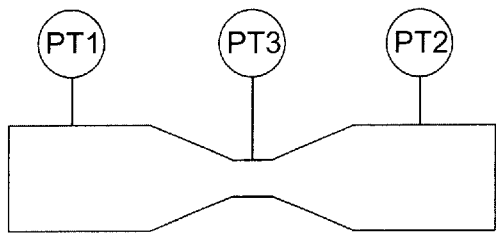
FIG. 4 is a diagrammatic illustration of a first alternative embodiment of the venturi metering device.
Figure 5:
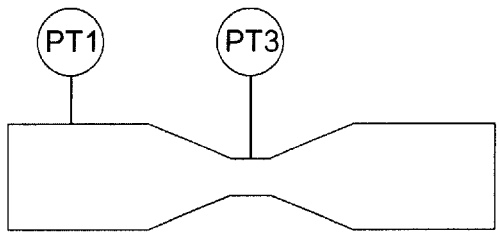
FIG. 5 is a diagrammatic illustration of a second alternative embodiment of the venturi metering device.
Figure 6:
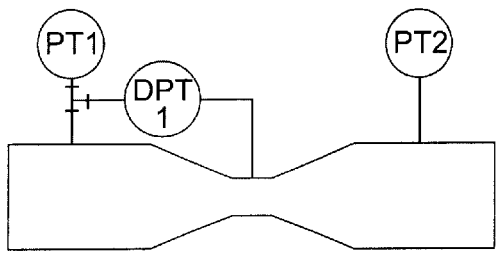
FIG. 6 is a diagrammatic illustration of a third alternative embodiment of the venturi metering device.
Figure 7:
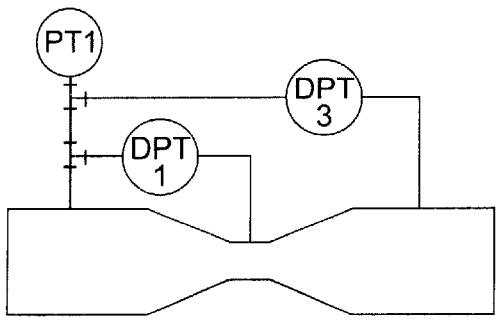
FIG. 7 is a diagrammatic illustration of a fourth alternative embodiment of the venturi metering device.

As shown in FIG. 4, the first and second differential pressure transducer DPT1 and DPT2 can be replaced by a third pressure transducers PT3. As shown in FIG. 5, one of the first or second pressure transducers PT1 or PT2 can actually be removed and the measurements can be replicated by the computer 50 based upon the readings received from the other sensors. As shown in FIGS. 6 and 7, the second differential pressure transducer DPT2 can be removed from the preferred embodiment; and furthermore, the second pressure transducer PT2 can be replaced with a third differential pressure transducer DPT3. These alternative embodiments, or other combinations that would be obvious to one skilled in the art, including mirror images and reversals of additions and replacements, should be considered within the scope of the claimed invention.

As shown in FIG. 1, the venturi metering device 30 further includes a temperature sensing means for sensing the temperature of the exhaust gas 14 passing through the venturi metering device 30, and for producing a second electrical output that characterizes the temperature that the temperature sensing means senses. In the preferred embodiment, the temperature sensing means includes a first temperature sensor T1, a second temperature sensor T2, and a third temperature sensor T3. The first temperature sensor T1 includes a first probe 52 that is operably positioned within the entrance section 34 through a first temperature sensing conduit 54. The second temperature sensor T2 includes a second probe 56 that is operably positioned within the exit section 38 through a second temperature sensing conduit 58. While only one of the first or second temperature sensors T1 or T2 is required for calculating the mass flow of the exhaust gas 14, the use of two sensors provides greater accuracy. The first and second temperature sensors T1 or T2 transmit the second electrical output to the computer 50 to enable the computer 50 to calculate the mass flow of the exhaust gas 14 through the venturi metering device 30.

The third temperature sensor T3 is operably connected to the housing 32 to sense the temperature of the housing 32. The third temperature sensor T3 is operably connected to transmit the second electrical output to the computer 50 to control the entrance and exit heaters 60 and 62, described below. The measurement of the temperature of the housing 32 by the third temperature sensor T3 also enables the computer 50 to determine the diameter of the throat section 36, correcting for the thermal expansion of the housing 32. Sensors such as the first temperature sensor T1, the second temperature sensor T2, and the third temperature sensor T3 are well known in the art, and various sensors and sensor arrangements can be devised by those skilled in the art without altering the invention.

The venturi metering device 30 further includes an entrance heater 60 operably positioned adjacent the entrance section 34, and an exit heater 62 operably positioned adjacent the exit section 38. The computer 50 is operably connected to the temperature sensing means, typically the third temperature sensor T3, so that the computer 50 can regulated the entrance and exit heaters 60 and 62. The entrance and exit heaters 60 and 62 are designed to vaporize any liquids, particularly any water that condenses from the exhaust gas 14, so that the venturi metering device 30 receives accurate measurements of the flow rate of the exhaust 14.

As shown in FIG. 2, the entrance section 34 and the exit section 38 preferably each include at least one annular condensation furrow 64 adjacent to the entrance and exit heaters 60 and 62, respectively. The at least one annular condensation furrow 64 of both the entrance and exit sections 34 and 38 function in conjunction with the entrance and exit heaters 62 to flash vaporize any condensed moisture that flows into the housing 32. While we describe this feature as a "furrow," it is equivalent to provide "ribs" that extend into the entrance and exit sections 34 and 38, thereby increasing the surface area and trapping condensation so that it can be flash vaporized.

As shown in FIG. 1, the apparatus 10 further includes a dilution air inlet 66 adapted to be connected with the exit section 38 to provide a mixture 18 of exhaust gas 14 and dilution air 16 that comes in through the dilution air inlet 66. The dilution air inlet 66 preferably includes a filter and other features (not shown), as described in Lewis et al., U.S. Pat. Nos. 5,184,501 and 6,122,980, and Lewis, U.S. Pat. Nos. 4,586,367, 4,660,408, and 4,823,591, the references being hereby incorporated by reference in full; however, since the structure of the dilution air inlet 66 is well known in the art, it is not described in greater detail herein. It is worth noting, however, that since the venturi metering device 30 provides an accurate measurement of the flow rate of the exhaust gas 14, it is not necessary for the dilution air inlet 66 to measure the flow rate of the dilution air 16. It is also worth noting that while the dilution air 16 is filtered atmospheric air in some embodiments, it is also possible to use a dry gas system as shown in FIG. 6 of Lewis et al, U.S. Pat. No. 5,184,501.

As shown in FIG. 1, the apparatus 10 further includes a flow confining path 68 for establishing a flow of the mixture 18 of the exhaust gas 14 and the dilution air 16 from the dilution air inlet 66 to a flow rate measuring means 70 for measuring the flow rate of the mixture 18. The flow confining path 68 including a sampling zone 72 from which a sampling means 74 can extract a sample of the mixture 18 as it flows through the sampling zone 72. The flow rate measuring means 70 can be any number of flow rate measuring devices well known in the art, including various venturi devices such as the venturi metering device 30 described above, or as shown in the prior art, including the Lewis references incorporated by reference.

Finally, the apparatus 10 further includes a flow control means 76 for controlling the flow of the mixture 18 from the flow confining path 68 through the flow rate measuring means 70 and out of the apparatus 10. As described in the Lewis references, and as well known in the prior art, the flow control means 76 can include a variable speed blower, a single speed blower and an adjustable valve, or any other equivalent mechanism known in the art.

The computer 50 is operably connected to the pressure sensing means of the venturi metering device 30 for computing the flow rate of the exhaust gas 14 through the venturi metering device 30 using the electrical output received from the pressure sensing means, using mathematical equations well known in the art. The computer 50 may also be operably connected to the flow rate measuring means 70 for measuring the flow rate of the mixture 18 in a similar manner. Finally, the computer 50 may be operably connected to the flow control means 76 for controlling the flow of the mixture 18 to maintain a preselected constant mass flow rate through the sampling zone 72. The general structure of this aspect of apparatus 10 is described in greater detail in Lewis et al., U.S. Pat. Nos. 5,184,501 and 6,122,980, and Lewis, U.S. Pat. Nos. 4,586,367, 4,660,408, and 4,823,591, the references being hereby incorporated by reference in full.

The computer 50 preferably further includes a register 65 and an A/D converter 66 for converting the electrical output of the pressure sensing means. The exhaust source 12 is connected to the entrance section 34 of the housing 32 so that the exhaust gas 14 from the exhaust source 12 flows into the entrance section 34, through the throat section 36, and out through the exit section 38 of the housing 32.

The A/D conversion rate of the A/D converter 66 is set to at rate that is high enough to characterize a waveform of the electrical output, preferably at least 200 conversions/second, although slower conversion rates can also provide an operative resolution. The A/D conversion rate must be high enough to take several readings per cycle of the exhaust source 12 being tested. The exhaust source 12 is typically an internal combustion engine of a motor vehicle, and the fastest generally used engine is a 4 cylinder that idles at 600 RPM (4 cycle). The idle pulsation frequency FREQ(i)=600 revolutions/minute*1 minute/60 seconds*2 pulses/revolution=20 pulses/second. If 10 samples are to be taken per pulsation, this results in the need of a minimum of 200 conversions per second. If the A/D conversion rate is high enough to accurately measure the flow rate at idle, when pulsation intensity is the most extreme, the A/D conversion rate will be high enough during other defined driving cycles. Obviously a smaller number of samples can be used at the expense of some accuracy, and 100 conversions/second is considered the slowest desirable conversion rate.

Once the exhaust source 12 is idling, a plurality of data points are read from the A/D converter 66, each of the plurality of data points representing the pressure values reported by the pressure sensing means. For each of the plurality of data points, a square root value is calculated and a result stored in the register 65. Once the register 65 is full, preferably with 20 readings, an average square root value is calculated from the sum of the results of the plurality of data points. Finally, an average flowrate is calculated from the average square root value using equations that are well known in the art.

This technique of calculating square root values of each of the plurality of data points is in sharp contrast to the prior art, which has always averaged the plurality of data points and then calculated the square root of the average. The methodology used in the prior art introduces errors due to the square root calculation, and the errors become significant when the venturi metering device 30 is positioned to record the pulsating flow of the exhaust gas 14 that is emitted by the exhaust source 12. The new method of calculation used in the present invention is one of the several innovations that enable the venturi metering device 30 to be positioned adjacent the exhaust source 12.

Figure 3:
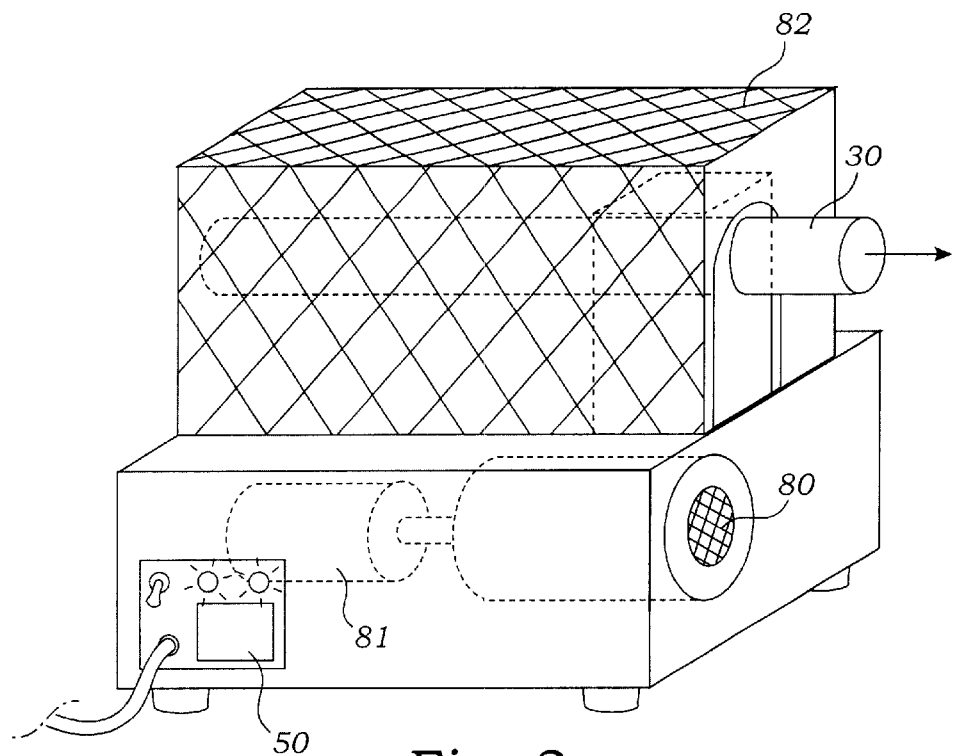
FIG. 3 is a perspective view of the apparatus.

In a first embodiment, as shown in FIG. 3, the venturi metering device 30 further includes a blower 80 and a heat shield 82. The blower 80 is operably attached to a variable speed blower controller 81 so that the strength of the blower 80 can be modulated to maintain the heat of the apparatus 10 within certain preset parameters. The heat shield 82 protects users from the heat associated with the exhaust gas 14.

Figure 9:
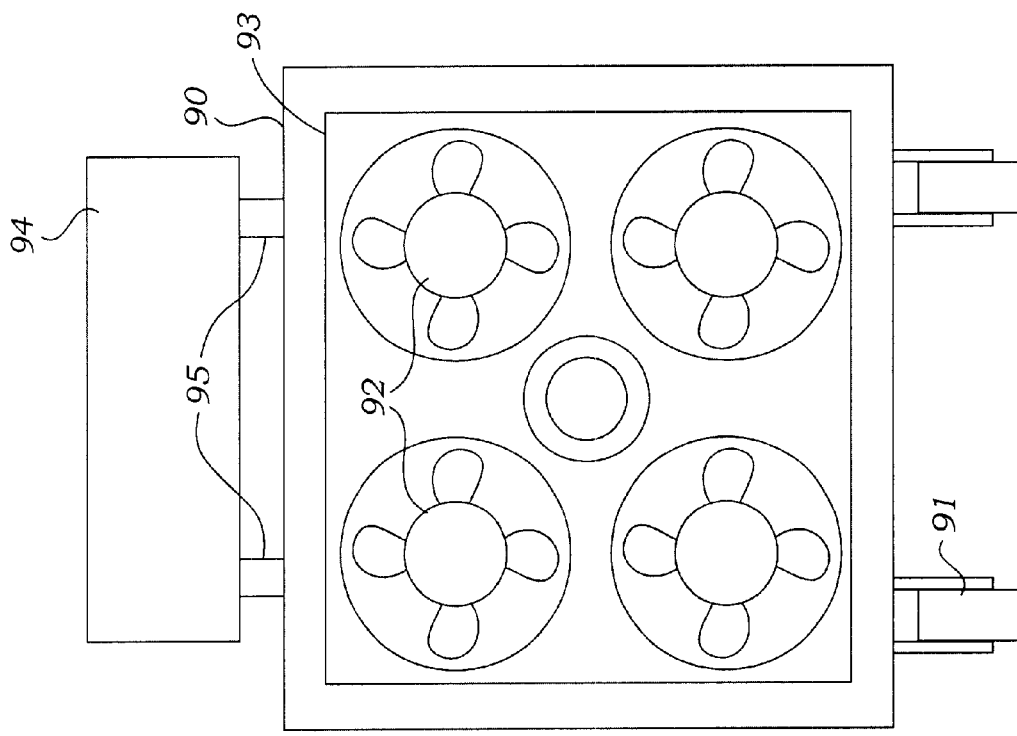
FIG. 9 is a front elevational view thereof
Figure 8:
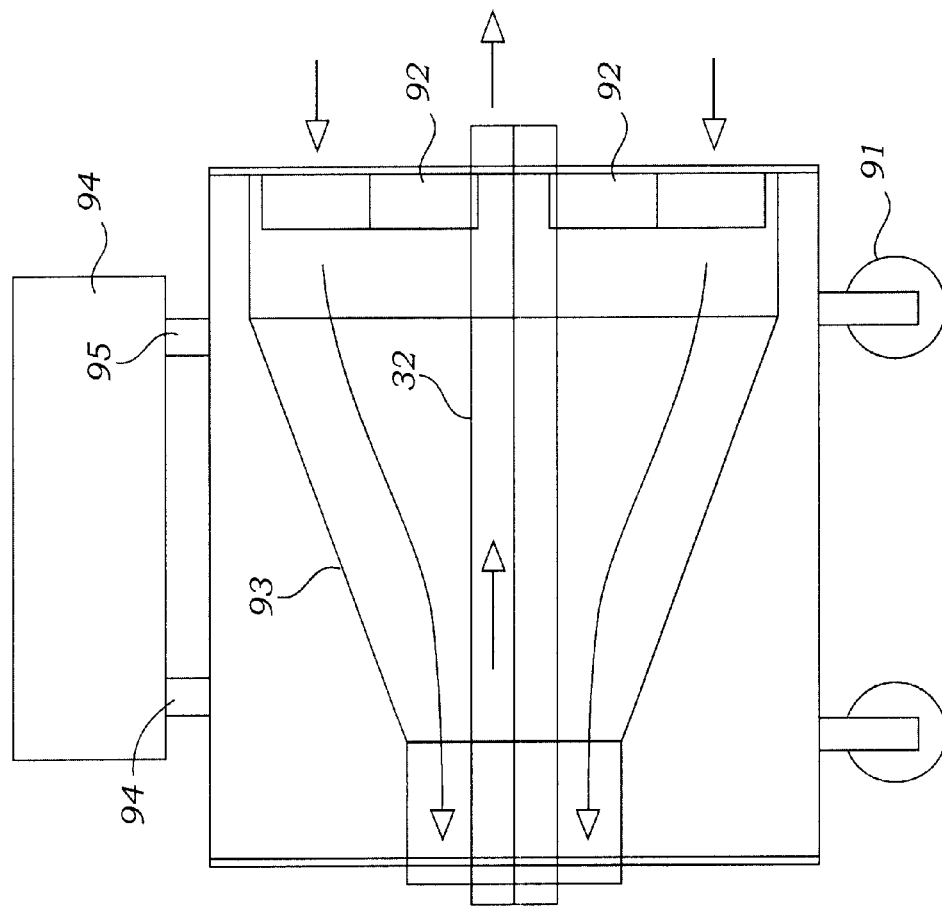
FIG. 8 is a side elevational view of a heat shield housing and an electronics box that house the venturi metering device.

In a second, preferred embodiment, as shown in FIGS. 8 and 9, the housing 32 of the venturi metering device 30 is positioned within a heat shielded housing 90 that is preferably supported by casters 91 or an equivalent support that provides for the mobility of the heat shielded housing 90. A fan means 92 is mounted adjacent the exit section 38 to blow air down the length of the housing 32. The fan means 92 is preferably a plurality of fans, most preferably 4 fans, although a single variable speed fan, as shown in FIG. 3, is also operable. The fan means 92 is preferably operably controlled by the computer 50 so that the strength of the fan means 92 is modulated to maintain the heat of the apparatus 10 within certain preset parameters. The housing 32 is preferably surrounded by a cowling 93 that directs the flow of air from the fan means 92 down the length of the housing 32.

As shown in FIGS. 8 and 9, the venturi metering device 30 preferably further includes an electronics box 94 separated from the heat shielded housing 90 with a plurality of spacers 95 to provide a protective air space between the electronics box 94 and the heat shielded housing 90. The electronics box 94 houses the first and second pressure transducers PT1 and PT2, the first and second differential pressure transducers DPT1 and DPT2, the first, second, and third temperature sensors T1, T2, and T3, the computer 50, and any other delicate electronics that might be used in conjunction with the venturi metering device 30.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A venturi metering device for measuring the flow of an exhaust gas in a conduit, the venturi metering device comprising:

a housing having a longitudinal axis, an entrance section, a throat section, and an exit section, the throat section having a smaller diameter than the entrance and exit sections;

a pressure sensing means for sensing the pressure in the throat section and the entrance section, and for producing an electrical output that characterizes the pressure that the pressure sensing means senses;

a computer for computing the flow rate through the housing using the electrical output, the computer being operably connected to the pressure sensing means for receiving the electrical output;

an entrance heater operably positioned adjacent the entrance section; and an exit heater operably positioned adjacent the exit section, the computer being operably connected to the entrance and exit heaters for controlling the temperature of the entrance and exit heaters to flash vaporize any condensed moisture that flows into the housing.

2. The venturi metering device of claim 1 wherein the entrance section and the exit section each including at least one annular condensation furrow adjacent to the entrance and exit heaters, respectively, the at least one annular condensation furrow of the entrance and exit sections functioning in conjunction with the entrance and exit heaters to flash vaporize any condensed moisture that flows into the housing.

3. The venturi metering device of claim 1 further comprising a temperature sensing means for sensing the temperature of the exhaust gas passing through the housing, and for producing a second electrical output that characterizes the temperature that the temperature sensing means senses, the computer being operably connected to the temperature sensing means for receiving the second electrical output.

4. The venturi metering device of claim 1 wherein the entrance section and the exit section are symmetrical about the throat section.

5. The venturi metering device of claim 1 further comprising:
the housing being contained in a heat shielded housing;
a fan means being mounted adjacent the exit section to blow air down the length of the housing; and
an electronics box having a plurality of spacers that are shaped to separate the electronics box from the heat shielded housing, the electronics box being adapted to contain the pressure sensing means and the computer.

6. The venturi metering device of claim 5 further comprising a cowling positioned within the heat shielded housing and around the housing, the cowling being shaped to direct the flow of air from the fan means down the length of the housing.

7. An apparatus for sampling the emission content of an exhaust gas from an exhaust source, the apparatus comprising:
an exhaust inlet adapted for connection with the exhaust source;
a venturi metering device for measuring the flow of the exhaust gas from the exhaust source, the venturi metering device having
a housing having a longitudinal axis, an entrance section, a throat section, and an exit section, the throat section having a smaller diameter than the entrance and exit sections, the entrance section being adapted for connection with the exhaust inlet;
a pressure sensing means for sensing the pressure in the throat section and the entrance section, and for producing an electrical output that characterizes the pressure that the pressure sensing means senses;
an entrance heater operably positioned adjacent the entrance section; and
an exit heater operably positioned adjacent the exit section;
a dilution air inlet adapted to be connected with the exit section to provide a mixture of exhaust and dilution air;
a flow confining path for establishing a flow of the mixture from the dilution air inlet to a flow rate measuring means for measuring the flow rate of the mixture, the flow confining path including a sampling zone;
a sampling means for extracting a sample of the mixture flowing through the sampling zone;
a flow control means for controlling the flow of the mixture out of the flow confining path; and
a computer operably connected to the pressure sensing means of the venturi metering device for computing the flow rate of the exhaust gas through the venturi metering device using the electrical output received from the pressure sensing means, the computer being operably connected to the flow rate measuring means for measuring the flow rate of the mixture, and the computer being operably connected to the flow control means for controlling the flow of the mixture to maintain a preselected constant mass flow rate through the sampling zone.

8. The apparatus of claim 7 wherein the entrance section and the exit section each include at least one annular condensation furrow adjacent to the entrance and exit heaters, respectively, the at least one annular condensation furrow of the entrance and exit sections functioning in conjunction with the entrance and exit heaters to flash vaporize any condensed moisture that flows into the housing.

9. The apparatus of claim 7 further comprising a temperature sensing means for sensing the temperature of the exhaust gas passing through the venturi metering device, and for producing a second electrical output that characterizes the temperature that the temperature sensing means senses, the computer being operably connected to the temperature sensing means for receiving the second electrical output.

10. A method for measuring the flow of an exhaust gas from an exhaust source, the method comprising the steps of:
providing a venturi metering device comprising:
a housing having a longitudinal axis, an entrance section, a throat section, and an exit section, the throat section having a smaller diameter than the entrance and exit sections;
a pressure sensing means for sensing the pressure in the entrance section and the throat section, and for producing an electrical output that characterizes the pressure that the pressure sensing means senses; and
a computer operably connected to the pressure sensing means for receiving the electrical output, the computer including a register and an A/D converter for converting the electrical output of the pressure sensing means;
providing an entrance heater adjacent the entrance section;
providing an exit heater adjacent the exit section;
connecting the exhaust source to the entrance section of the housing so that the exhaust gas from the exhaust source flows into the entrance section, through the throat section, and out through the exit section of the housing;
setting the A/D conversion rate to a rate that is high enough to characterize a waveform of the electrical output;
reading a plurality of data points from the A/D converter, and for each of the plurality of data points calculating a square root value and storing a result in the register;
calculate an average square root value from the sum of the results of the plurality of data points; and
calculating an average flowrate from the average square root value.

11. The method of claim 10 wherein the entrance section of the housing is attached so close to the exhaust source that pulsation from the engine periodically creates a reverse flow within the housing.

12. The method of claim 10 wherein the A/D conversion rate is high enough to take several readings per cycle of the exhaust source.

13. The method of claim 10 wherein the A/D conversion rate is at least 100 conversions per second.

14. The method of claim 10 wherein the A/D conversion rate is at least 200 conversions per second.

15. The method of claim 10 further comprising the step of heating the entrance heater and the exit heater to a temperature that is great enough to vaporize any liquid that condenses from the exhaust gas.

16. The method of claim 10 further comprising the steps of: measuring the temperature of the housing; and correcting the measurement of the average flowrate based upon the thermal expansion of the housing.

* * * * *